United States Patent [19]

Fu et al.

[11] Patent Number: 5,733,726

[45] Date of Patent: Mar. 31, 1998

[54] CYTOTOXICITY-BASED GENETIC SELECTION SYSTEM (TOXSEL)

[75] Inventors: Haian Fu, Atlanta, Ga.; R. John Collier, Wellesley, Mass.; Raymond Dingledine, Athens, Ga.

[73] Assignees: Emory University, Atlanta, Ga.; President and Fellows of Harvard College, Cambridge, Mass.

[21] Appl. No.: 472,238

[22] Filed: Jun. 7, 1995

[51] Int. Cl.$^6$ .............................. C12Q 1/68; C12N 1/19; C12N 15/79

[52] U.S. Cl. .................... 435/6; 435/254.2; 435/320.1

[58] Field of Search ..................... 435/6, 172.3, 320.1, 435/254.2

[56] References Cited

U.S. PATENT DOCUMENTS

| | | |
|---|---|---|
| 5,080,898 | 1/1992 | Murphy ............................ 424/94.1 |
| 5,283,173 | 2/1994 | Fields et al. .......................... 435/6 |

FOREIGN PATENT DOCUMENTS

| | | |
|---|---|---|
| WO 95/26400A1 | 5/1995 | WIPO . |

OTHER PUBLICATIONS

Wilson et al. (1993) A genetic method for defining DNA-binding domains: application to the nuclear receptor NGFI-B. Proc. Natl. Acad. Sci. USA 90:9186-9190, Oct. 1993.

Mendelsohn et al. (1994) Applications of interaction traps/two-hybrid systems to biotechnology research, Curr. Opin. Biotechnol. 5:482-486, Mar. 1994.

Luban et al., "The yeast two-hybrid system for studyikng protein-protein interactions," *Current Opinion in Biotechnology* (1995) 9:58-64.

Fields, S. and Song, O-k, "A novel genetic system to detect protein-protein interactions," Nature (1989) 340:245-246.

Celenza, J.L. and Carlson, M., "A Yeast Gene That Is Essential for Release from Glucose Repression Encodes a Protein Kinase," Science (1986) 233:1175-1180.

Chien, C-T et al., "The two-hybrid system: A method to identify and clone genes for proteins that interact with a protein of interest," Proc. Natl. Acad. Sci. USA (1991) 88:9578-9582.

Durfee, T. et al., "The retinoblastoma protein associates with the protein phosphatase type 1 catalytic subunit," Genes & Development (1993) 7:555-569.

Gyuris, J. et al., "Cdi1, a Human G1 and S Phase Protein Phosphatase That Associates with Cdk2," Cell (1993) 75:791-803.

Vojtek, A.B. et al., "Mammalian Ras Interacts Directly with the Serine/Threonine Kinase Raf," Cell (1993) 74:205-214.

Fearon, E.R. et al., "Karyoplasmic interction selection strategy: A general strategy to detect protein-protein interactions in mammalian cells," Proc. Natl. Acad. Sci. USA (1992) 89:7958-7962.

Fields, S. and Sternglanz, R., "The two-hybrid system: an assay for protein-protein interactions," Trends in Genetics (1994) 10:286-292.

Vasavada, H.A. et al., "A contingent replication assay for the detection of protein-protein interactions in animal cells," Proc. Natl. Acad. Sci. USA (1991) 88:10686-10690.

Brent, R. and Ptashne, M., "A Eukaryotic Transcriptional Activator Bearing the DNA Specificity of a Prokaryotic Repressor," Cell (1985) 43:729-736.

Harper, J.W. et al., "The p21 Calk-Interactinng Protein Cip1 Is a Potent Inhibitor of G1 Cyclin-Dependent Kinases," Cell (1993) 75:805-816.

Ausubel, F.M. et al., "Interaction Trap/Two-Hybrid System to Identify Interacting Proteins," Current Protocols in Molecular Biology, Wiley, New York, NY, 1987.

*Primary Examiner*—George C. Elliott
*Assistant Examiner*—Robert Schwartzman
*Attorney, Agent, or Firm*—Greenlee, Winner and Sullivan

[57] ABSTRACT

The invention provides a cytotoxicity-based genetic selection (TOXSEL) method and related testing kit for the identification and positive selection of molecules or mutations that are capable of disrupting a specific protein—protein interaction. The invention enables positive selection of molecules disruptive of specific protein—protein interactions by virtue of the presence in the TOXSEL system of a toxin reporter gene. A disrupted protein—protein interaction precludes expression of the toxin reporter gene and, consequently, allows survival of the host cell. TOXSEL technology enables large-scale screening for drugs or small molecules capable of disrupting specific protein—protein interactions critical in processes such as cellular signalling, carcinogenesis, etc. The positive selection of molecules or mutations capable of interfering with specific protein—protein interactions permits the identification of amino acid residues or motifs critical in the protein—protein interactions and permits the design of drugs for therapeutic or diagnostic applications.

16 Claims, 5 Drawing Sheets

Functional Transcriptional Activator (FTA)
activating transcription of a detectable reporter gene Two hybrid proteins and a detectable gene construct Interaction between two hybrid proteins and
activation of transcription

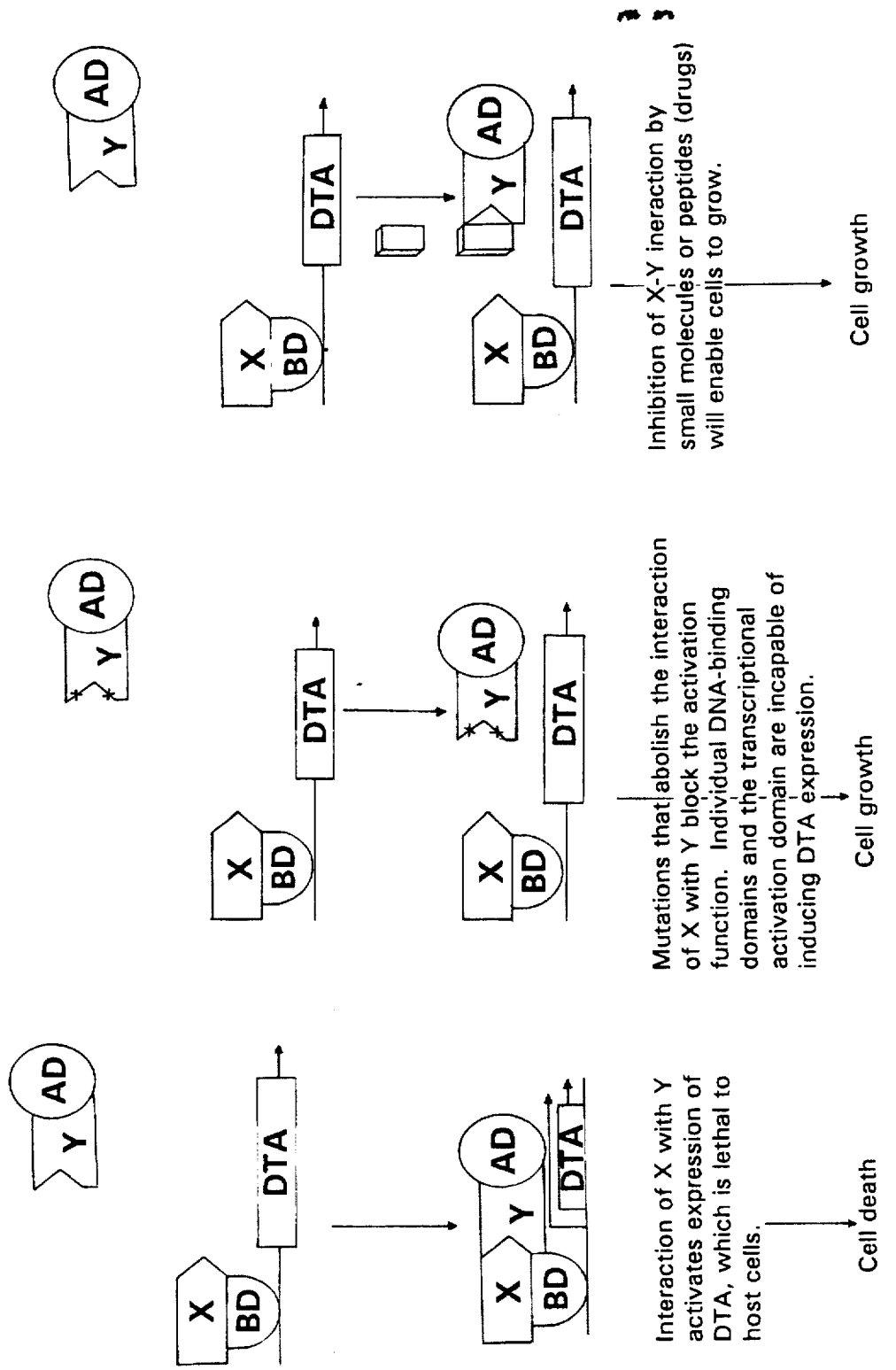

GAL4 (1-881)  | BD                              AD |
              1-147                       768-881

Functional GAL4 Transcriptional Activator

FIG. 4A

GAL4(1-147)-SNF1  | BD         SNF1          |
                  1-147
                        GAL4-X hybrid

FIG. 4B

SNF4-GAL4(768-881)  | SNF4             AD |
                                    768-881

GAL4-Y hybrid

FIG. 4C

GAL1-DTA gene  ─────UAS$_G$─────| DTA |─────

Unactivated gene construct with toxic reporter gene

FIG. 4D

CYTOTOXICITY-BASED GENETIC SELECTION SYSTEM (TOXSEL)

The invention was partially made with Government support under Grant No. AI22021 awarded by the National Institutes of Health.

The United States Government has certain rights in this invention.

FIELD OF THE INVENTION

The invention relates generally to a cytotoxicity-based genetic selection technology or system (TOXSEL) that permits the positive identification of critical residues involved in specific protein—protein interactions and that provides a simple assay for the positive selection of drugs or mutations that specifically interfere with these protein—protein interactions.

BACKGROUND OF THE RELATED ART

Protein-protein interactions between two proteins have traditionally been studied using biochemical techniques such as cross-linking, co-precipitation and co-fractionation. Fields and Song (1989) Nature 340:245–246 developed a genetic system to study protein—protein interactions by utilizing a pair of interacting proteins, i.e., proteins that comprise two separable and functionally essential domains. In particular, Fields and Song (1989) Supra utilized the GAL4 protein of *Saccharomyces cerevisiae*, a transcriptional activator required for the expression of genes encoding enzymes necessary for galactose metabolism. The GAL4 protein consists of two interacting protein domains: an N-terminal domain which binds to specific DNA sequences (UAS$_G$) but fails to activate transcription and a C-terminal domain which contains the activating regions but which cannot activate transcription because it fails to localize to UAS$_G$.

The GAL4 protein domains were each hybridized to a protein, for example, the GAL4 DNA-binding domain was fused to a protein X and the GAL4 activating region was fused to a protein Y. When X and Y form a protein—protein complex in such a manner that proximity of the GAL4 domains are reconstituted, transcription of a gene regulated by the GAS$_G$ occurs. This genetic system was exemplified (Fields and Song (1989) supra) using as proteins X and Y two yeast proteins known to interact—SNF1 and SNF4 (Celenza and Carlson (1986) Science 233:1175–1180). High transcriptional activity was obtained only when both hybrids were present in a cell.

This genetic system is useful generally to identify proteins that interact with a known protein by the use of a simple galactose selection. For example, yeast containing a known protein as a GAL4 hybrid would be transformed with a clone bank of genomic or complementary DNA sequences fused to the GAL4 activating region. The double transformants would be selected for ability to grow on galactose or screened for blue color on indicator plates for those able to express the β-galactosidase gene. Thus, yeast cells containing the interacting hybrid proteins can be detected easily against a background of cells which contain a non-interacting proteins and are white.

The idea of a two-hybrid system and the experimental demonstration of its feasibility are important for two reasons. First, the use of the translational activation domain on the interacting protein increases the likelihood that its binding to the DNA-bound protein will detectably increase transcription of the reporter. Second, it was demonstrated that transcription can be used as a tool to study interactions between proteins not involved in the transcription process. Recent two-hybrid systems [Chien et al. (1991) Proc. Natl. Acad. Sci. 88:9578–9582; Durfee et al. (1993) Genes Dev. 7:555–569; Gyuris et al. (1993) Cell 75:791–803; Vojtek et al. (1993) Cell 74:205–214; Fearon et al. (1992) Proc. Natl. Acad. Sci. 89:7958–7962; and Fields et al. (1994) Trends Genet. 10:286–292] for detecting intracellular protein—protein interactions make use of these phenomena (Field and Song 1989 supra).

None of the aforementioned art suggests a genetic selection system to detect protein—protein interactions in vivo that is linked to the transcriptional activation of a toxic reporter gene, providing not only an assay sensitive for protein—protein interaction but also a simple assay for positive selection of mutations or small molecule inhibitors or drugs disruptive of protein—protein interactions.

Accordingly, a need remains for such a genetic assay system and related testing kit for positive selection of mutations or small molecules or drugs that interfere with specific protein—protein interactions.

SUMMARY OF THE INVENTION

It is an object of the invention to provide a cytotoxicity-based genetic selection (TOXSEL) method and related testing kit to identify and select positively for molecules or mutations that are capable of disrupting a specific protein—protein interaction.

The invention provides a TOXSEL system in which molecules are positively selected for their ability to disrupt a specific protein—protein interaction based on the survival of host cells. The TOXSEL system of the invention utilizes a reporter gene encoding a toxin gene. Successful interaction between two interacting proteins results in expression of the toxin and cell death. Disruption of the specific protein—protein interaction precludes toxin production and results in survival of the host cells.

It is another object of the invention to provide molecules or mutations identified by the TOXSEL technology as being capable of disrupting a specific protein—protein interaction. TOXSEL-identified molecules have utility as therapeutic and/or diagnostic agents and as affinity reagents for protein purification. TOXSEL-identified mutations are useful in the design of drug and genetic therapies for the control of diseases.

It is a further object of the invention to employ TOXSEL technology to screen large numbers of molecules for those having the capability to interfere with specific protein—protein interactions and to utilize such molecules identified by TOXSEL as drugs for therapeutic, pharmaceutical or diagnostic applications.

It is another object of the invention to utilize TOXSEL technology to positively identify critical amino acid residues or motifs involved in protein—protein interactions.

It is yet another object of the invention to provide a method which can be used in the design of peptides or drugs to be used therapeutically, pharmaceutically or diagnostically.

It is a further object of the invention to provide a TOXSEL system for testing affinity reagents for protein purification.

The invention provides a method and a kit utilizing a cytotoxicity-based genetic selection (TOXSEL) technology that permits positive selection of molecules that specifically disrupt or block the protein—protein interactions and the use of these molecules as drugs for diagnosis or treatment of diseases or conditions involving the protein—protein interaction.

The TOXSEL technology further provides a method for identifying and positively selecting molecules or mutations disruptive of the specific protein—protein interaction by virtue of the presence in the TOXSEL system of a toxin reporter gene. In the TOXSEL technology of the invention, a positive protein—protein interaction results in the expression of the encoded toxin and leads to the death of the host cell. A disrupted or blocked protein—protein interaction precludes expression of the toxin reporter gene and, consequently, allows the host cell to survive. Thus, the TOXSEL technology is used in the invention to identify only those molecules or mutations that do disrupt or block specific protein—protein interactions. The positive selection of such molecules or mutations capable of interfering with specific protein—protein interactions permits the identification of amino acid residues or motifs critical in the specific protein—protein interactions.

One advantage of the TOXSEL method of the invention is that a multiplicity of molecules or mutations can be easily tested to determine whether any are capable of disrupting a known protein—protein interaction. Inactive molecules or mutations are lost with the demise of the host cells. Active molecules or mutations, on the other hand, are positively selected in the TOXSEL assay, for the survival of the host cells, in itself, is the immediate indicator that the test molecule has the capability of disrupting a protein—protein interaction.

Additional advantages of this invention include its variable sensitivity and the ability to examine disruption of specific protein—protein interactions in an in vivo environment. Since positive selection is determined from the survival of host cells comprising active molecules or mutations, the TOXSEL system is not only expedient and easy to perform, but is flexible so that the disruption of protein—protein interactions can be examined under conditions affording differing stringencies, for example, by controlling the nature of the toxin reporter gene and its relative cytotoxicity.

The invention provides a TOXSEL method useful in the discovery of drugs capable of interfering with known protein—protein interactions in therapeutic, pharmaceutic or diagnostic applications. For example, the TOXSEL method may be used to discover drugs that prevent specific cell-surface receptor and toxin or growth factor or antigen interactions or drugs that inhibit protein—protein interactions involving an oncogene/proto-oncogene-encoding product.

In a particular example, TOXSEL-identified molecules may disrupt a specific interaction between a protein expressed from an oncogene (e.g., a protein kinase) and its target protein, the specific interaction being associated with the advent of neoplastic transformation. In another example, TOXSEL-identified molecules may disrupt a specific protein—protein interaction occurring when a virus infects a cell by recognizing a particular cell surface receptor; such TOXSEL-identified molecules may be used to design antiviral agents.

Thus, the invention also provides a TOXSEL system useful in the design of drugs capable of interfering with known protein—protein interactions in therapeutic, pharmaceutic or diagnostic applications.

The invention further provides a TOXSEL method useful in testing affinity reagents for protein purification. Peptides or protein domains can be identified that interact with a known protein of interest and these may then be used in a purification protocol for the known protein.

BRIEF DESCRIPTION OF THE DRAWINGS

FIGS. 1A. represents a functional transcriptional activator activating transcription of a detectable reporter gene. FIG. 1B. represents two hybrid proteins and a detectable gene construct. FIG. 1C. represents interaction between two hybrid proteins and the activation of transcription. AD=transcriptional activation domain; BD=DNA-binding domain; UAS=upstream activation site.

FIG. 2A–2C exemplifies schematically the cytotoxicity-mediated genetic selection technology (TOXSEL). In this system, the cytotoxic protein, DTA, is used as a reporter. Activation of DTA expression by specific protein—protein interactions (X–Y as shown here) leads to cell killing (FIG. 2A) while mutations (FIG. 2B) or inhibitors (FIG. 2C) that sufficiently attenuate the interaction of X with Y may abolish the production of DTA and allow host cells to grow. As shown herein, TOXSEL provides positively identified mutations and positively selected inhibitors critical for a specific protein—protein interaction. (DTA=diphtheria toxin catalytic A fragment; AD=DNA-binding domain; AD=transcriptional activation domain).

FIGS. 4A–4D presents schematically plasmid constructs described in Example 1.

DETAILED DESCRIPTION OF THE INVENTION

Figure 1A:
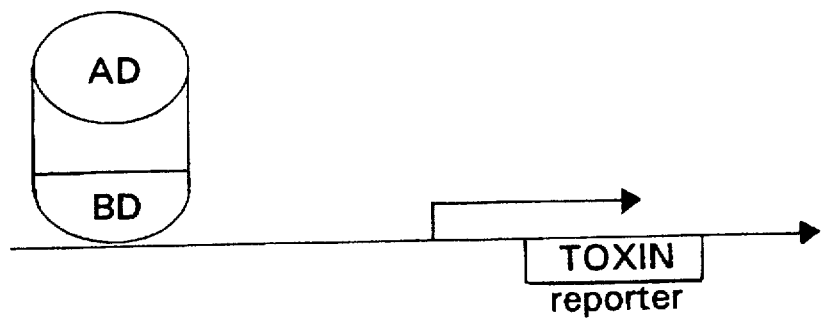
FIGS. 1A–1C represents schematically transcriptional activation of a gene by reconstitution of a transcriptional activator.

The following definitions are given in order to provide clarity as to the intent or scope of their usage in the specification and claims.

The terms cytotoxicity-based genetic selection technology or system or TOXSEL as used herein refer to a genetic system for studying specific protein—protein interactions linked to the expression of a toxin reporter gene permitting positive selection of molecules or mutations disruptive of the specific protein—protein interactions. The TOXSEL technology of the invention is used to identify only those molecules or mutations that disrupt a specific protein interaction, since the disruption of the specific interaction precludes the expression of the toxin gene and results in the survival of the host cell; successful protein—protein interaction leads to death of the host cell.

The terms transcriptionally activating or transcriptional activation as used herein refer to the activation of gene transcription which occurs when an amino acid sequence comprising a transcriptional activation domain of a transcriptional activator is in sufficient proximity to a detectable reporter gene.

The term different selection stringencies as used herein refers to the different conditions which may be used to carry out the TOXSEL technology in order to maximize positive selection. For example, reporter genes having different cytotoxicities, different induction conditions, etc., may be utilized to achieve assay conditions of different stringencies.

The term molecule as used herein refers to an organic molecule, native or synthetic, including but not limited to a peptide, nucleic acid, carbohydrate, lipid, or combinations thereof, capable of disrupting a specific protein—protein interaction in the TOXSEL technology. A protein refers to a molecule having the entire amino acid sequence of the protein or to an active fragment thereof, i.e., a fragment, derived from the protein, that has essentially the same activity as the whole protein.

The term a test molecule as used herein refers to a molecule that is being tested in the TOXSEL technology to determine if it is capable of disrupting a specific protein—protein interaction.

The term a drug as used herein refers to any molecule, other than food or a device, that is intended for use in the diagnosis, cure, mitigation, treatment or prevention of disease, or is intended to affect the structure or any function of the body of man or other animals.

The term vector as used herein refers to any polynucleotide construct capable of encoding the cis-acting regulatory sequence and the effector gene(s) selected, and capable of transferring these genes into suitable target cells. Vectors may be linear or circular, double-stranded or single-stranded. Vectors may comprise DNA, RNA, DNA/RNA hybrids, and DNA and/or RNA polynucleotides having chemically modified bases. Suitable vectors within the scope of this invention include linear dsDNA segments, plasmids, recombinant viruses, etc.

The terms specific protein—protein interaction or specific interaction between a first interacting protein and a second interacting protein or protein X-protein Y interaction as used herein refer to the chemical interactions between proteins that enable two or more proteins to associate. Specific protein—protein interactions are involved, for example, in the assembly of enzyme subunits; in antigen-antibody reactions; in forming the supramolecular structures of ribosomes, filaments, and viruses; in transport; and in the interaction of receptors on a cell with growth factors and hormones. Products of oncogenes can give rise to neoplastic transformation through protein—protein interactions. For example, some oncogenes encode protein kinases whose enzymatic activity on cellular target proteins leads to the cancerous state. Another example of a protein—protein interaction occurs when a virus infects a cell by recognizing a polypeptide receptor on the surface, and this interaction has been used to design antiviral agents.

The term mutation as used herein refers to modification(s) in the amino acid sequence of one of the interacting proteins. Such modifications include, for example, addition, deletion or substitution of amino acid residues. It is recognized in the art that certain modifications are more likely to yield equivalent activity than others. Substitution of negatively charged for negatively charged, positively charged for positively charged, aromatic for aromatic all have a higher likelihood of success than nonsimilar substitutions. The operating principles for choosing the most probable active equivalents are well-known in the art and active equivalents can be found according to the teachings herein without undue experimentation. Additions and deletions can also yield active equivalents. Truncated or internally deleted peptides comprising at least a portion of the protein sequence can be made without undue experimentation following the teachings of the invention together with the prior art. It is contemplated that mutant proteins are engineered through modification of the corresponding genes [Ausubel et al. (1987) *Current Protocols in Molecular Biology* (Wiley, New York, N.Y.); Deng et al. (1992) Anal. Biochem. 200:81–88].

A method based on a cytotoxicity-based genetic selection technology (TOXSEL) is provided herein for the positive identification of critical amino acid residues/motifs involved in specific protein—protein interactions and for the positive selection of molecules that specifically disrupt or block the interactions.

Two classes of reporter genes are currently employed to detect protein—protein interactions in yeast: nutritional markers, such as leu2 and his, for growth selection and lacZ for color visualization. For mammalian cells, markers, such as bacterial chloramphenicol acetyltransferase, cell-surface CD4, and hygromycin B resistance gene, have been used. In these systems, protein—protein interaction leads to the expression of reporter genes, resulting in growth on nutritional deficient, or drug containing media, or color production in indicator plates. These reporters are ideal for studying positive protein—protein interaction.

The TOXSEL technology differs from above systems in that a cytotoxic reporter is used which, when expressed, produces a toxin that kills the host cell. In a specific embodiment, the diphtheria toxin gene is used as the toxic reporter. Any mechanisms (mutations or drugs) that effectively disrupt the specific interaction will enable host cells to grow. These mutants directly involved in protein—protein interactions or small molecules that disrupt these interactions will be identified from growing cells. Therefore, TOXSEL provides a direct positive selection for mutations or small molecules that disrupt the specific protein—protein interactions. These mutations may reveal molecular targets for drug intervention or structure based drug design; and the selected small molecules may become the basis for drug development.

The TOXSEL technology of the invention provides a simple, positive selection for mutations or small molecules that affect specific protein—protein interactions, because disruption of the specific protein—protein interactions is coupled to host cell growth. Because diphtheria toxin is lethal to all eukaryotic cell types tested, this TOXSEL system is applicable to all eukaryotic cells, including yeast and mammalian cells and is not restricted to specified growth conditions in the way nutritional reporters usually are. Additional advantages of the TOXSEL technology include:

(a) TOXSEL is a simple assay because cell growth is the indicator for effective molecules, drugs or mutations. This property is amenable to automation of the manipulation.

(b) The test for cytotoxicity of test drugs is built into this selection system because only non-toxic drugs enable the host cell to survive; toxic inhibitors kill the host cells during the selection process.

(c) The test for the effectiveness of drug delivery is also built into this selection system, because successful drugs must not only be able to disrupt the protein—protein interactions, but must also be able to penetrate cells. Drugs that can not penetrate into host cells are not able to block the lethal effect of the expressed toxin.

(d) Drugs identified by this selection scheme necessarily disrupt the functional interaction between two target proteins (with appropriate controls), so that the mechanism of action is indicated or suggested a priori. This saves time in drug development.

The TOXSEL technology may be applied to any biological system comprising specific protein—protein interactions, for example, in disease processes, such as, cancer, etc. In such applications, TOXSEL can be used to: (a) define critical residues/motifs directly involved in protein—protein interactions for mechanistic studies; (b) identify specific targets for drug intervention and structure-based drug design; (c) select for small molecules, including natural products, peptides and nucleic acids, for drug development; and (d) modify this cytotoxicity-based concept in order to study protein-DNA interactions and to identify new drugs that disrupt specific protein-DNA interactions.

The basic strategy of the TOXSEL technology is shown in FIG. 1. FIG. 1A schematically illustrates the binding of a functional transcriptional activator (FTA), having a DNA-binding domain (BD), and a transcriptional activator domain (AD). The functional transcriptional activator binds to a specific DNA sequence designated UAS (upstream activating sequence) [West et al. (1984) Mol. Cell Biol. 4:2467-2478] and activates transcription of a reporter gene in a gene construct carrying the reporter gene. Transcriptional activation of the reporter gene is indicated by the arrow. In a specific embodiment, the functional transcriptional activator is a GAL4 protein which contains two separate domains—a DNA-binding domain and a transcriptional activator domain—and is a potent activator of transcription of a GAL1-toxic reporter gene when yeast are grown on galactose media. In another embodiment of the invention, a preferred transcriptional activator comprises a DNA-binding domain that is a native *E. coli* LexA repressor protein. Gene activation and DNA binding by Drosophil Ubx and abd-A proteins [Samson et al. (1989) Cell 57:1045-1052] is also contemplated by the invention.

Figure 1B:
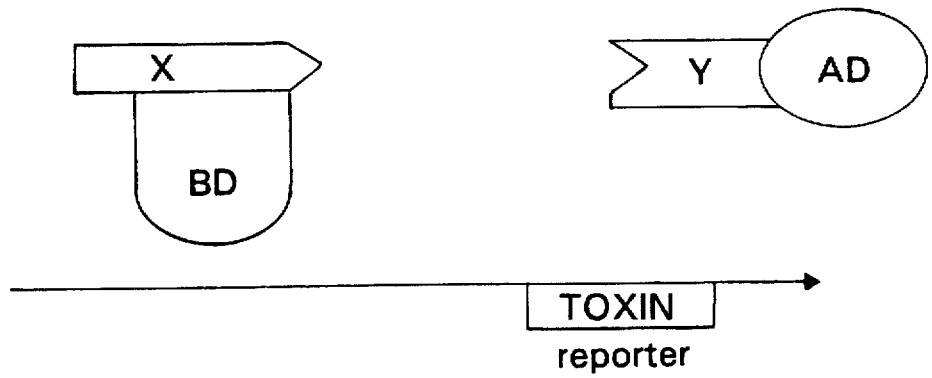

FIG. 1B schematically illustrates two hybrid proteins and a detectable gene construct. A first hybrid protein comprises one of the interacting proteins (protein X) and the DNA-binding domain, (BD). A second hybrid protein comprises a second interacting protein (protein Y) and a transcriptional activation domain (AD). Neither of these hybrid proteins alone is able to activate transcription.

Figure 1C:
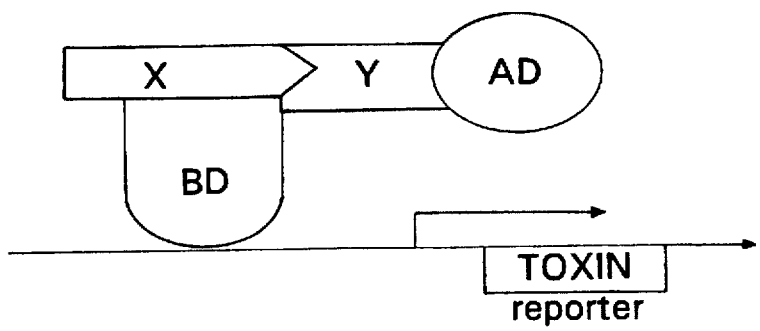

FIG. 1C schematically illustrates the interaction between proteins X and Y, as a consequence of which, the transcriptional activation domain (AD), is brought into sufficient proximity to the DNA-binding domain, (2D) to activate transcription of the detectable reporter gene and to produce toxin which is lethal to the host cell.

The system is dependent on a number of conditions to properly carry out the method of this invention. The first interacting protein X must not, itself, carry an activation domain for the reporter. Otherwise the activation domain would allow transcription of the reporter gene as soon as the vector encoding only the DNA-binding domain fused to the first interacting protein X is introduced. The interaction between protein X and protein Y must be capable of occurring within the nucleus. The activation domain portion of the hybrid containing protein Y must be accessible to the transcription machinery of the cell to allow transcription of the marker gene. The activation domain is brought to close proximity of the promoter by the specific interaction between proteins X and Y. Should any of these conditions not exist, the system may be modified by constructing hybrids that carry only portions of the interacting proteins X and Y using art-known methods [Ausubel et al. (1987), supra] and thus meet these conditions.

Since other eukaryotic cells can utilize a yeast transcription system, eukaryotic cells such as HeLa cells, COS cells, NIH3T3 cells or other mammalian cells can be used instead of yeast to test for protein—protein interactions. The toxic reporter gene function can be serviced by any of a large variety of toxin genes known to the art. The function of a transcriptional activator can be served by any transcriptional activator that has separable domains for DNA-binding and for transcriptional activation. Indeed, any protein, even one that is not a transcriptional activator, that has two separable functions can be used to establish a similar genetic system to detect protein—protein interactions, although it is preferred to couple the specific protein—protein interaction with two separate domains of a transcriptional activator.

Molecules to be tested for their capability to disrupt a specific protein—protein interaction using the TOXSEL system are introduced into the host cell using art-known methods, e.g., diffusion, polyethylene glycol method, liposomes, electroporation, particle bombardment, gene gun, etc. Generally, test molecules can be added to the TOXSEL incubation medium and allowed to penetrate the host cell. However, a molecule that does not readily penetrate the host cell may also be tested in the TOXSEL system. For example, the permeability of cells, for example, yeast, can be increased by selection of appropriate mutants (Sclafani et al. (1986) Genetics 114:753-767; Lawrence (1991) in *Guide to Yeast Genetics and Molecular Biology* (Guthrie and Fink, eds.) Academic Press Inc. Harcourt Brace Jovanovich, Publishers, San Diego Calif. 92101, pp. 273-281), by treatment with lytic enzymes to dissolve the cell wall (Hinnen et al. (1978) Proc. Natl. Acad. Sci. 75:1929-1933) or by treatment with specific reagents, such as polymixin B [Boguslawski et al. (1985) Mol. Gene Genet. (1985) 199:401]. If the test molecule is a protein, it is possible to evaluate the test protein in the TOXSEL system by introducing into the host cell a plasmid comprising a gene encoding the protein to be tested, if the gene corresponding to the test protein is known.

In accordance with the present invention, the method includes providing a eukaryotic host cell, preferably a yeast cell, for example, *Saccharomyces cerevisiae* or *Schizosaccharomyces pombe*. This invention also contemplates the use of mammalian cells, for example, CHO cells, COS cells, HeLa cells, NIH 3T3 cells, Rat1 cells, etc., in particular for the positive selection and/or discovery of small molecule inhibitors or drugs capable of interfering with specific protein—protein interactions in humans. The ability to interface different eukaryotic components in the design of two hybrid genetic selection systems has been demonstrated, e.g., Gyuris et al. (1993) Cell 75:791-803; Vasavada et al. (1991) Proc. Natl. Cad. Sci. 88:10686-10690; Fearon et al. (1992) Proc. Natl. Acad. Sci 89:7958-7962. An interacting protein may be a bacterial protein, viral protein, oncogene/proto-oncogene-encoded protein, growth factor, receptor protein, regulatory protein (e.g., GTP-binding protein), and enzyme. Examples of specific interacting proteins include, but are not limited to, the Ras-Raf proteins [Vojtek et al. (1993) Cell 74:205-214], the SNF4-SNF1 proteins [Fields and Song (1989) Nature 340:245-246], the retinoblastoma protein—protein phosphatase type 1 catalytic subunit [Durfee et al. (1993) Genes and Dev. 7:555-569], Cdil-Cdk2 proteins (Gyuris et al. (1993) Cell 75:791-803].

In the invention, the host cell contains a detectable gene comprising a binding site for the DNA-binding domain of the transcriptional activator, such that the detectable gene expresses a detectable protein when the detectable gene is transcriptionally activated. Such activation occurs when the transcriptional activation domain of a transcriptional activator is brought into sufficient proximity to the DNA-binding domain of the transcriptional activator. The detectable gene further comprises a reporter gene encoding a toxin which is expressed when the detectable gene is activated transcriptionally. The detectable gene may also comprise enhancer sequences or other such transcription activating sequences that allow increased levels of transcription and, where desired, tissue targeting sequences, for example the nucleus localization signal (Mendelsohn and Brent (1994) supra).

The host cell also includes a promoter in the detectable gene capable of directing the expression of the reporter gene. The promoter may be viral, bacterial or eukaryotic. It is preferred that a strong promoter be used in the TOXSEL system to allow synthesis of proteins in amounts sufficient to enable protein—protein interaction and transcriptional activation of reporter gene expression.

Promoters utilized in the plasmids/vectors carrying genes encoding the hybrid proteins of the invention may be the same as or different from the promoter used in the detectable gene. If an inducible promoter is utilized, it is preferred that the other promoters in the system, and not the promoter of the reporter gene, be inducible.

The invention also provides a first chimeric gene encoding a first hybrid protein comprising a DNA-binding domain that recognizes the binding site on the detectable gene in the host-cell. The first hybrid protein also contains a first interacting protein (protein X) which interacts specifically with a second interacting protein (protein Y). Also provided is a second chimeric gene which comprises a DNA sequence that encodes a second hybrid protein. The second hybrid protein comprises a transcriptional activator domain as well as a second interacting protein (protein Y) which interacts specifically with protein X.

Preferably, the DNA-binding domain of the first hybrid protein and the transcriptional activation domain of the second hybrid protein are derived from transcriptional activators having separate DNA-binding and transcriptional activation domains. Such transcriptional activators having separate DNA-binding and transcriptional activation domains are known in the art and include, but are not limited to, the yeast GAL4, GCN4 and ADR1 proteins, the *E. coli* repressor LexA, and mammalian variants of VP16 [Fearon et al. (1992) Proc. Natl. Acad. Sci. 89:7958–7962 and Vasavada et al. (1991) Proc. Natl. Acad. Sci. 88:10686–10690]. Many other proteins involved in transcription also have separable DNA-binding and transcriptional activation domains which make them useful for carrying out the present invention as suggested in Fields et al. (1994) Trends Genet. 10:286–292. It is also contemplated by the invention that the DNA-binding domain and the transcriptional activation domain may be from different transcriptional activators.

The first and second chimeric genes of the invention are capable of being expressed in the host cell. In one embodiment, both the first and second chimeric genes are introduced into the host cell in the form of plasmids. In another embodiment, the first chimeric gene is present in a chromosome of the host cell and the second chimeric gene is introduced into the host cell as part of a plasmid. Both first and second chimeric genes may comprise genomic, cDNA or synthetically generated DNA sequences encoding the protein sequences making up the transcriptional activator and/or the interacting X and Y proteins. Examples of two-hybrid systems describing different X-Y protein interactions are found in, for example, Chien et al. (1991) Proc. Natl. Acad. Sci. 88:9578–9582; Dalton et al. (1992) Cell 68:597–612; Durfee et al. (1993) Genes Dev. 7:555–569; and Vojtek et al. (1993) Cell 74:205–214.

The interaction between the first interacting protein (protein X) and the second interacting protein (protein Y) in the host cell causes (i) reconstitution of the transcriptional activator protein and (ii) activation of the transcription of the detectable gene. The method is carried out by introducing the first chimeric gene and the second chimeric gene into the host cell. The host cell is subjected to conditions under which the first hybrid protein and the second hybrid protein are expressed in sufficient quantity for the detectable gene to be activated.

The detectable gene in the TOXSEL system is a toxic reporter gene. Transcriptional activation of the detectable gene leads to the synthesis of a toxin which is immediately detected by the cytotoxic death of the host cell.

In a specific embodiment of the invention, the toxic reporter gene encodes the diphtheria toxin catalytic fragment (DTA). As illustrated in FIG. 2, this system uses the modular nature of transcription activators to detect protein—protein interactions. As exemplified in this system, a first plasmid carries a chimeric gene encoding the DNA-binding domain (BD) of the *E. coli* repressor LexA fused to a first interacting protein (X). A second plasmid carries a chimeric gene encoding a transcriptional activation domain (AD) fused to a second interacting protein (Y). Expression of the activation domain alone is not sufficient to activate the expression of the toxin reporter gene, because of the lack of the DNA binding function. The interaction of LexA-X with an interacting-protein, Y, that is fused to the activation domain, brings LexA and the activation domain into proximity, thereby reconstituting the transcriptional activation function and inducing expression of the toxin reporter gene.

When expressed in eukaryotic cells, DTA is lethal to the host because it ADP-ribosylates elongation factor-2 and inhibits protein synthesis. Thus, interaction of protein X (as an activation domain fusion) with protein Y (as a sequence-specific DNA binding domain fusion) induces the expression of the toxic reporter protein, DTA, leading to death of the host cells (FIG. 2A). Mutations (FIG. 2B) or small molecules (FIG. 2C) that sufficiently attenuate the interaction of proteins X and Y will impair expression of DTA, thereby permitting host cells to grow. In this way, amino acid residues or small molecule inhibitors critical to specific interaction of any two proteins may be identified from surviving cells.

Figure 3:
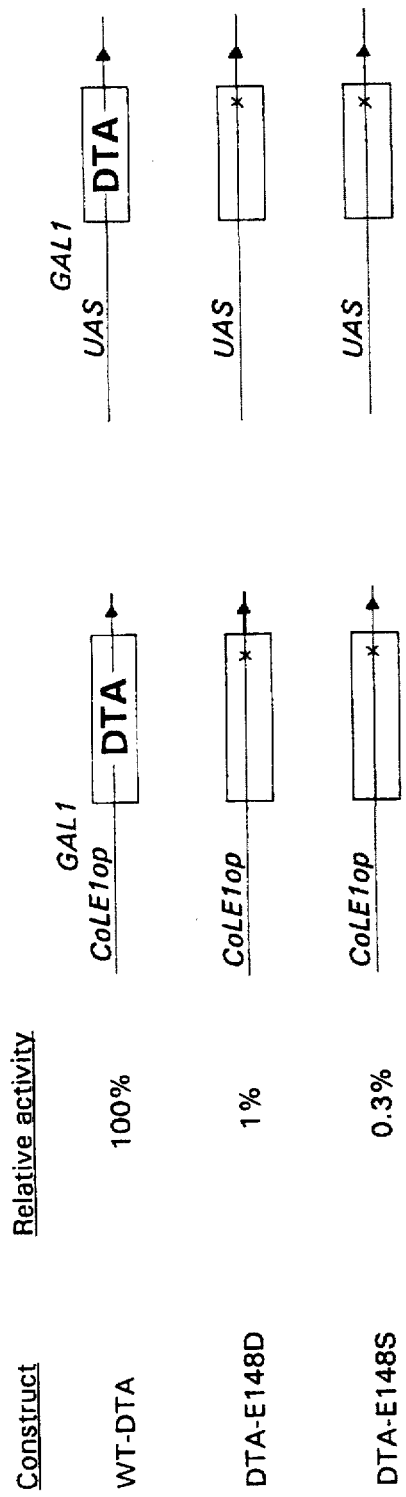
FIG. 3 presents DTA-based cytotoxic reporters for TOXSEL systems. ColE1op=LexA binding site of colicin E1 gene; UAS=upstream activating sequence in GAL1 promoter.

In a specific embodiment of the invention, the TOXSEL system features reporter genes with varying degrees of cytotoxicity to permit different selection stringencies (FIG. 3) and to ensure the success of the positive selection feature. The diphtheria toxin catalytic domain is used as a primary toxic reporter because its structure and mechanism of cytotoxicity is well understood in the art. Various mutants of DTA differing in catalytic activity are known in the art [Wilson et al. (1990) Biochemistry 29:8643–8651] and can be utilized in the TOXSEL system as primary toxic reporters. For example, FIG. 3 provides a wide panel of reporter gene constructs comprising DTA mutants encoding DTA derivatives exhibiting varying DTA activities. These constructs are prepared as described in Ausubel et al. (1987) supra. Plasmids comprising these constructs are available as reported in Wilson et al. (1987) supra. Similar constructs carrying DTA mutants can be prepared for use in mammalian cells using art known methods, for example, Ausubel et al. (1987) supra. In principle, any toxic protein can be used for this purpose, for example, ricin, exotoxin A of *Pseudomonas aeruginosa*, and Shiga toxin.

The method of the present invention as described herein may be practiced using a kit for the positive selection of a molecule that disrupts or blocks a specific protein—protein interaction. The kit includes a container, two vectors, and a host cell. The first vector contains a promoter and may include a transcription termination signal functionally associated with the first chimeric gene in order to direct the transcription of the first chimeric gene. The first chimeric gene includes a DNA sequence that encodes a DNA-binding domain and a unique restriction site(s) for inserting a DNA sequence encoding a first interacting protein in such a manner that the first interacting protein is expressed as part of a hybrid protein with the DNA-binding domain. The first vector also includes a means for replicating itself in the host cell and in bacteria. Also included on the first vector is a first gene, the expression of which in the host cell permits selection of cells containing the first marker gene from cells that do not contain the first marker gene. Preferable, the first vector is a plasmid.

The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second interacting protein into the vector, in such a manner that the second interacting protein is capable of being expressed as part of a hybrid protein with the transcriptional activation domain. Preferably, the DNA-binding domain of the first hybrid protein and the transcriptional activation domain of the second hybrid protein are derived from transcriptional activators having separate DNA-binding and transcriptional activation domains.

The second vector further includes a means for replicating itself in the host cell and in bacteria. The second vector also includes a second marker gene, the expression of which in the host cell permits selection of cells containing the second marker gene from cells that do not contain the second marker gene.

The kit includes a host cell, preferably a yeast strain of *Saccharomyces cerevisiae* or *Schizosaccharomyces pombe* or a mammalian cell. The host cell contains the detectable gene comprising a binding site for the DNA-binding domain of the first hybrid protein, a promoter, and a primary reporter gene that is a toxin gene. The binding site is positioned so that the detectable gene expresses a toxin when the detectable gene is activated by the transcriptional activation domain encoded by the second vector. Activation of the detectable gene is possible when the transcriptional activation domain is in sufficient proximity to the detectable gene. The host cell, by itself, is incapable of expressing a protein having a function of the first marker gene, the second marker gene, the DNA-binding domain, or the transcriptional activation domain.

The cells containing the two hybrid proteins are incubated in an appropriate medium and the culture is monitored for the detectable activity. When the first interacting protein and the second interacting protein have interacted, such interaction brings the DNA-binding and transcriptional activation domains of the transcriptional activator into sufficiently close proximity to cause transcription of the reporter gene. Activation of the detectable gene carrying a toxic reporter gene results in the expression of the toxin which leads to the death of the host cell.

Accordingly, in using the kit to test for the capability of a molecule to interfere with the protein—protein interaction, the molecule to be tested is introduced (either directly or, in the case of a protein, as a plasmid comprising a gene encoding the protein to be tested) into the host cell before the specific protein—protein interaction is allowed to occur. When the molecule is inactive, i.e., does not interfere with the specific protein—protein interaction, expression of the detectable gene is activated, toxin is produced and the host cell dies. However, if the molecule disrupts or blocks the specific protein—protein interaction, transcription of the detectable reporter gene is not activated, toxin is not produced and the host cell survives. Thus, molecules that are active, i.e., capable of interfering with the specific protein—protein interaction, are positively selected for, using this TOXSEL method of the present invention.

Accordingly, the TOXSEL method of the present invention can be applied more generally to any molecule capable of disrupting a specific protein—protein interaction. This general embodiment of the present invention positively selects for a molecule disrupting a specific protein—protein interaction and permits the positive identification of critical amino acid residues or motifs involved in the protein—protein interaction. The TOXSEL method permits not only detection of a specific protein—protein interaction but, more importantly, also permits identification of drugs that cause the disruption of the specific interaction.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the functional features of the molecules described herein and how to employ those alternatives to achieve functional equivalents of the molecules of the present invention. It is intended that the present invention include those variants, modifications, alternatives, and equivalents which are appreciated by the skilled artisan and encompassed by the spirit and scope of the present disclosure.

The following examples are provided to better elucidate the practice of the present invention and should not be interpreted in any way to limit the scope of the present invention. Those skilled in the art will recognize that various modifications can be made to the methods and formulations described herein while not departing from the spirit and scope of the present invention.

EXAMPLE 1

Exemplification of TOXSEL technology using GAL4 as the transcriptional activator and the diphtheria toxin catalytic domain as the primary toxic reporter.

(a) Detection of interaction between proteins X and Y

The method and components of the kit of the present invention are exemplified using GAL4 as the transcriptional activator, SNF1 and SNF4 as the two interacting yeast proteins, X and Y, and the diphtheria toxin catalytic domain as the primary toxic reporter. High transcriptional activity is obtained only when the SNF1-GAL4 (DNA-binding domain) hybrid and the SNF4-GAL4 (transcription activating domain) interact, bringing into close proximity the two domains of the transcriptional activator. This proximity is sufficient to cause transcription, which is detected by the activity of the reporter gene, expressing diphtheria toxin which is lethal to the eukaryotic host cells.

The SNF1 protein is a serine-threonine specific protein kinase, as reported by Celenza and Carlson in *Scientists* (1986), 233:1175–1180. The SNF4 protein is physically associated with SNF1 and is required for its maximal activity, see Celenza and Carlson, *Molecular and Cellular Biology*, 9, 5034–5044 (1989) and Celenza, Eng, and Carlson, *Molecular and Cellular Biology*, 9, 5045–5054 (1989).

The relevant constructs of the interacting hybrid proteins used in this example are illustrated in FIG. 4 and include some of the constructs described in Fields and Song (1989) supra. FIG. 4A illustrates the entire GAL4 protein of 881 amino acids (Laughton et al. (1984) Mo. Cell. Biol. 4:260–264), designated GAL4 (1–881) and comprising at the N-terminus a DNA-binding domain, "BD," which is capable of binding to the GAL upstream activation site (UAS$_G$) [Keegan et al. (1986) supra] and at the C-terminus a transcriptional activation domain, "AD." FIG. 4B illustrates a GAL4-X protein hybrid between GAL4(1–147), the DNA-binding domain of GAL4, fused in frame to the entire coding sequence (633 amino acids) of the SNF1 protein (Celenza and Carlson (1986) supra). FIG. 4C illustrates a GAL4-Y protein hybrid designated SNF4-GAL4 (768–881) between the SNF4 (minus the last amino acid of the protein sequence as per Celenza et al. (1989) supra) fused in frame to a GAL4 activation domain. This GAL4 activation domain is sufficient when fused to the GAL4 DNA-binding domain to induce transcription of the GAL4 gene (Ma and Ptashne (1987) Cell 48:847–853). FIG. 4D illustrates a GAL1DTA fusion gene where DTA represents a diphtheria toxin catalytic A domain as the primary toxic reporter. Expression of DTA activity is a measure of GAL4 function derived from the plasmid-borne GAL4 constructs.

The DNA sequence GAL4 (1–881) is carried on plasmid pCL1; GAL4 (1–147) is carried on plasmid pMA424; GAL4 (1–147) SNF1 is carried on plasmid pEE5; SNF4 is carried on plasmid pFF1; and SNF4-GAL4 (768–881) is carried on plasmid pNI12. Methods for constructing these plasmids carrying specific proteins of the GAL4-X-Y system are described in Fields and Song U.S. Pat. No. 5,283,173, issued Feb. 1, 1994.

Plasmids carrying the individual GAL4 constructs are introduced into strain GGY1::171 (Gill and Ptashne (1987) Cell 51:121–126), which is deleted for both GAL4 and GAL80 and which contains a GAL1-DTA fusion gene integrated at the URA3 locus. Thus, DTA activity is a measure of GAL4 function derived from the plasmid-borne GAL4 constructs. The strain also contains mutations of the HIS3 and LEU2 genes, which are the selectable genes on plasmids containing the DNA-binding and activation domains, respectively.

Transformants are grown in media which can induce transcription from $UAS_G$. Media containing 2% galactose, 2% ethanol, and 2% glycerol, but not leucine or histidine, or both, are appropriate in order to maintain the plasmids.

A plasmid containing a functional GAL4 construct exhibits DTA activity, as judged by cell death. The DNA-binding domain GAL4 (1–147), the GAL4 (1–147)-SNF1 hybrid protein, and the SNF4-GAL4 (768–881) hybrid protein, individually, fail to activate transcription. However, when plasmids encoding GAL4 (1–147)-SNF1 and SNF4-GAL4 (768–881) are both introduced, DTA activity is detected, as judged by the resultant cytotoxicity.

Thus, yeast cells containing the interacting hybrid proteins, which interaction results in the production of DTA activity, are immediately identified through cytotoxicity. Accordingly, any disruption of the interaction between the hybrid proteins results in the attenuation or abolition of expression of DTA activity and thus survival of the host yeast cells.

(b) Positive Selection of Molecules Attenuating the Interaction Between Proteins X and Y.

The TOXSEL system as described above is used according to this invention to identify and to positively select for molecules (amino acid residues, small molecule inhibitors, etc.) that interfere with the protein—protein interaction between proteins X and Y. In this system, the gene encoding a toxin, e.g. DTA, is used as a reporter. When expressed in eukaryotic cells, DTA is lethal to the host. Interaction of protein X (e.g. SNF1) with protein Y (e.g. SNF4) induces the expression of the toxin, DTA, leading to death of the host cells. Molecules that interfere with the X-Y protein interaction impair the expression of DTA, thereby permitting the host cells to grow. In this way, molecules critical to a specific interaction between any two proteins are identified and positively selected for from the survival of the host cells comprising these molecules.

In carrying out the TOXSEL assay for positive selection, it is necessary to determine the appropriate conditions for ensuring that a specific interaction between proteins X and Y is occurring, as judged by the expression of the DTA reported gene and as evidenced by host cell death. Then, under the same assay conditions which allow X-Y protein interaction, a test molecule is introduced together with the interacting protein components of the assay into the host cells. If the test molecule is inactive and does not interfere with the X-Y interaction, the host cell dies. However, if the test molecule is active and interferes with the specific interaction between proteins X and Y, the host cell survives. This TOXSEL method can also be carried out in essentially the same way to screen a battery or panel of test molecules in order to expedite the screening process for active drugs. In this manner, this method selects positively for only those host cells harboring molecules capable of critically interfering with a specific interaction between protein X and protein Y.

EXAMPLE 2

TOXSEL technology exemplified using LexA as the DNA-binding domain of a transcriptional activator and the diphtheria toxin catalytic domain as the primary toxic reporter.

The TOXSEL technology is carried out essentially as described in Example 1, except that the GAL4 transcriptional activator is replaced with a native E. coli LexA repressor protein [Gyuris et al. (1993) Cell 75:791–803; Vojtek et al. (1993) Cell 74:205–214], which binds tightly to appropriate operators [Colemis et al. (1992) Mol. Cell. Biol. 12:3006–3014; Ebina et al. (1983) J. Biol. Chem. 258:13258–13261] and carries a dimerization domain at its carboxy terminus. In yeast, LexA and most LexA derivatives enter the nucleus [Brent et al. (1985) Cell 43:729–736; Brent et al. (1984) Nature 312:612–615].

In a particular example, a first chimeric gene comprising a LexA-protein X first hybrid protein is expressed in yeast, is verified not to stimulate transcription, and is determined to bind operator by performing a "repression" assay [Brent et al. (1984) Nature 312:612–615]. Once these conditions are established, the first chimeric gene and a second chimeric gene encoding a second hybrid protein including an activation domain and protein Y are introduced into a yeast host cell comprising a detectable gene comprising a LexA operator and a toxin reporter gene to create a positive selection strain. The host cell is incubated as described above in Example 1 in the presence and absence of a test molecule which is evaluated for its ability to disrupt the specific interaction between proteins X and Y. Positive selection for molecules able to disrupt the protein interaction is made on the basis of cell survival.

In addition to the LexA system, other DNA-binding domains have been identified which can be used in the TOXSEL system of the invention [Chien et al. (1991) Proc. Natl. Acad. Sci. 88:9578–9582; Durfee et al. (1993) Genes 7:555–569; Harper et al. (1993) Cell 75:805–816]. These systems contain the DNA-binding domain of the GAL4 protein, encoded by residues 1–147. This region is sufficient for tight binding to appropriate DNA-binding sites and for localizing fused proteins to the nucleus.

EXAMPLE 3

Exemplification of TOXSEL technology using the Ras and Raf proteins as the specific interacting proteins, LexA-transcriptional activation domain as the transcriptional activator and diphtheria toxin catalytic domain as the primary toxic reporter.

The TOXSEL technology is carried out essentially as described in Example 1, except that the GAL4 transcription activator is replaced by a LexA-B42 transcription activator [Ausubel et al. (1987) supra] and the SNF4-SNF1 proteins are replaced by a Ras-Raf interacting protein pair. The Ras protein is a guanine nucleotide-binding protein [Lowy et al. (1993) Ann. Rev. Biochem. 62:851-891] that binds to a Raf protein [Howe et al. (1992) Cell 71:335-342], forming a bimolecular complex [Moodie et al. (1993) Science 260:1658-1661; Vojtek et al. (1993) Cell 74:205-214; Zhang et al. (1993) Nature 364:308-313; Warne et al. (1993) Nature 364:352-355].

Figure 5:
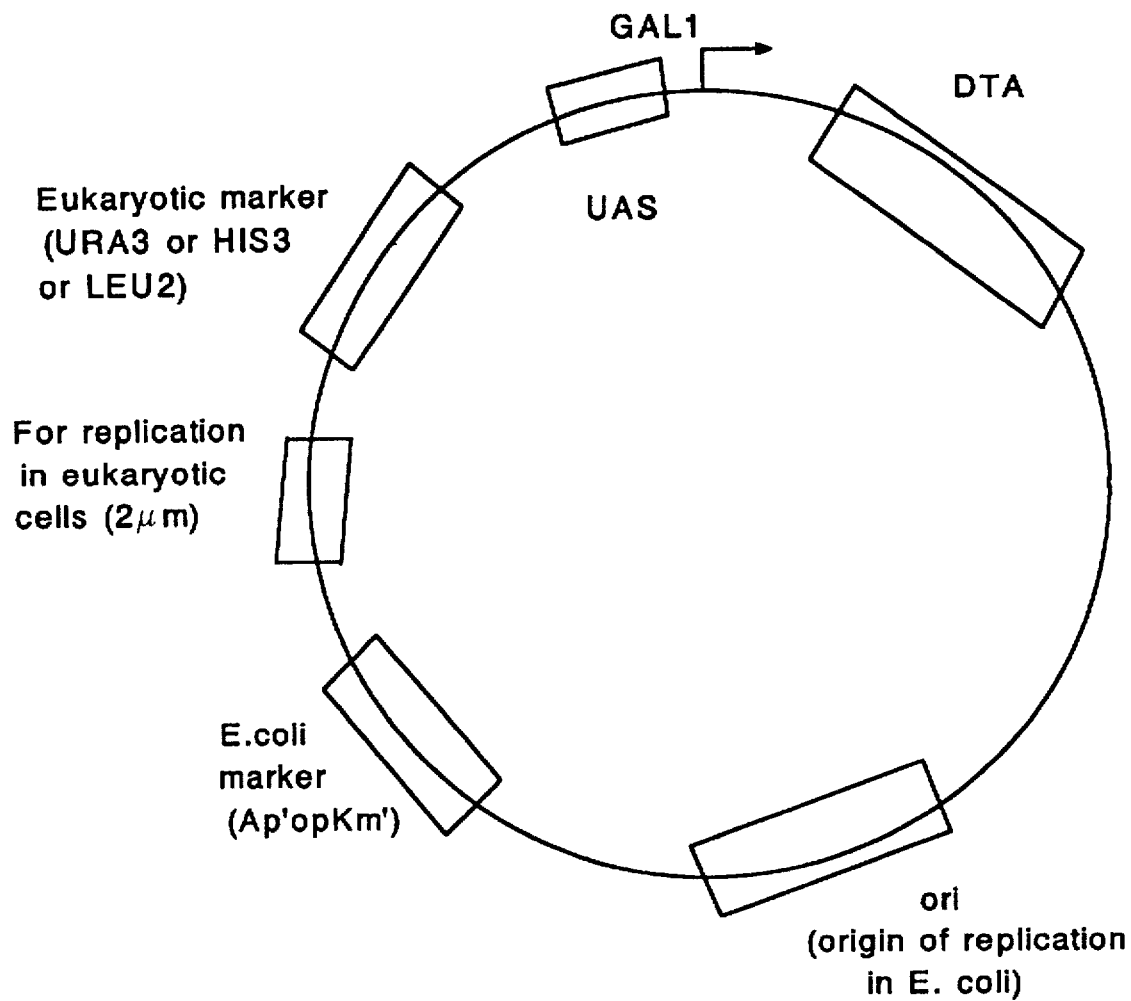
FIG. 5 presents schematically an example of a TOXSEL reporter plasmid.

The Ras protein is fused to the LexA-DNA binding domain in a first plasmid [Ausubel et al. (1987) supra]; constitutive expression of this fusion is reported in Gyuris et al. (1993) supra. The Raf protein is fused to the B42 activation sequence in a second plasmid. Expression of the B42-Raf hybrid is under the control of the GAL1 promoter and is induced by the addition of galactose to the medium. A third plasmid comprises a reporter gene encoding DTA placed under the control of a modified GAL1 promoter comprising the ColE1 operator sequence from *E. coli* (a LexA binding sequence) (see FIG. 5). The yeast host is transformed with these three plasmids under non-inducing conditions. Galactose induction of the Ras-Raf interaction specifically activates the expression of DTA, leading to cell death.

In order to identify mutations in Ras, the Ras gene is randomly mutagenized in the plasmid (e.g., by biological or chemical mutagens) before the transformation. After the mutagenized pools of Ras gene in the plasmid are introduced into the host strain harboring the B42-Raf plasmid and the reporter gene construct, cells are plated on galactose containing plates. Galactose induces the expression of B42-Raf which interacts with LexA-Ras. LexA-Ras binds to the ColE1 site of the reporter gene, bringing the B42 transcriptional activation domain into sufficient proximity to activate transcription, leading to the expression of DTA. Normal Ras-Raf interaction kills cells; mutations in Ras that sufficiently attenuate the interaction of Ras with Raf allows host cells to grow and form colonies. The plasmid harboring mutations in Ras is isolated and the mutation is mapped by sequencing. The identified region may become the target for drug intervention because any means that can disrupt Ras-Raf interaction in vivo may provide an opportunity for developing anti-cancer drugs.

For drug discovery, the TOXSEL procedure is performed in 96-well plates or other multiple well apparatus to facilitate large scale selection of drugs. Cells containing all components of the system (LexA-Ras, B42-Raf and the DTA reporter) are distributed into each well containing inducing medium (e.g., galactose). A library of test drugs/small molecules is introduced into each well by a multi-channel pipetter. After incubation, cell growth is measured by a plate reader. Growing cells are selected and the test molecules applied to those specific wells identified. These procedures are repeated to confirm the specific disruption of Ras-Raf interaction by the identified molecules.

What is claimed is:

1. A cytotoxicity-based genetic selection (TOXSEL) method for the positive selection of a molecule or a mutation that disrupts a specific protein—protein interaction between a first interacting protein and a second interacting protein, said method comprising the steps of:

(a) providing a host cell containing a detectable gene, said gene comprising:
  (i) an upstream activation site for binding a DNA-binding domain;
  (ii) a promoter; and
  (iii) a reporter gene encoding a protein which is a toxin, said toxin being expressed upon transcriptional activation of said detectable gene, said transcriptional activation occurring when an amino acid sequence comprising a transcriptional activation domain is in sufficient proximity to said detectable gene;

(b) providing a first chimeric gene which is expressed in the host cell, said first chimeric gene comprising a DNA sequence encoding a first hybrid protein comprising:
  (i) said DNA-binding domain recognizing said upstream activation site on said detectable gene in the host cell; and
  (ii) a first interacting protein which interacts specifically with a second interacting protein;

(c) providing a second chimeric gene which is expressed in the host cell, said second chimeric gene comprising a DNA sequence encoding a second hybrid protein comprising:
  (i) said transcriptional activation domain; and
  (ii) said second interacting protein which interacts specifically with said first interacting protein;

(d) introducing said first chimeric gene and said second chimeric gene into the host cell;

(e) subjecting the host cell to conditions allowing said first hybrid protein and second hybrid protein to be expressed in quantities sufficient to allow specific interaction between said first interacting protein and said second interacting protein resulting in the positioning of said transcriptional activation domain in sufficient proximity to said detectable gene so that said detectable gene is transcriptionally activated to cause expression of said toxin reporter gene, resulting in death of the host cell; or (f) introducing into the host cell a molecule to be tested for its capability to disrupt said interaction between said first interacting protein and said second interacting protein; and (g) subjecting the host cell to conditions
  (i) allowing said first hybrid protein and said second hybrid protein to be expressed in quantities sufficient to allow specific interaction between said first interacting protein and said second interacting protein such that transcription is activated, said toxin is expressed and said host cell dies if said test molecule is not capable of disrupting said protein—protein interaction, and
  (ii) allowing said test molecule, if it is capable of doing so, to disrupt said interaction between said first interacting protein and said second interacting protein, thereby disrupting transcriptional activation of said detectable gene, which disrupts expression of said toxin reporter gene, and results in survival of the host cell.

2. The method according to claim 1 wherein said host cell is a eukaryotic cell.

3. The method according to claim 1 wherein said toxin is selected from the group consisting of diphtheria toxin, ricin, exotoxin A of *Pseudomonas aeruginosa* and Shiga toxin.

4. The method according to claim 1 wherein said DNA-binding domain and said transcriptional activation domain are from different transcriptional activators.

5. The method according to claim 1 wherein said first interacting protein or second interacting protein is selected from the group consisting of bacterial protein, viral protein, oncogene/proto-oncogene-encoded protein, growth factor, receptor protein, regulatory protein and enzyme.

6. The method according to claim 1 wherein said first hybrid protein or second hybrid protein is encoded on a library of plasmids comprising DNA inserts selected from the group consisting of genomic DNA, cDNA and synthetic DNA.

7. The method according to claim 1 wherein said chimeric genes are introduced into the host cell in the form of plasmids.

8. The method according to claim 1 wherein said first chimeric gene is integrated into the chromosomes of the host cell.

9. The method according to claim 2 wherein said host cell is a yeast cell or a mammalian cell.

10. The method according to claim 3 wherein said toxin is a diphtheria toxin catalytic A fragment or a toxic mutant thereof.

11. The method according to claim 4 wherein said transcriptional activators are bacterial, viral or eukaryotic.

12. The method according to claim 11 wherein said transcriptional activators are selected from the group consisting of yeast GAL4, yeast GCN4, yeast ADR1 and *E. coli* LexA repressor protein.

13. A kit for the positive selection of a molecule which disrupts a specific protein—protein interaction between a first interacting protein and a second interacting protein, comprising a container, three vectors and a host cell, said first vector comprising a promoter transcribing a first chimeric gene comprising a DNA sequence encoding a first hybrid protein including a DNA-binding domain and a first interacting protein, said second vector comprising a promoter transcribing a second chimeric gene comprising a DNA sequence encoding a second hybrid protein including a transcriptional activation domain and a second interacting protein, said host cell comprising a third vector comprising a detectable gene, said detectable gene comprising a binding site for said DNA-binding domain of said first hybrid protein, a promoter, a reporter gene encoding a protein which is a toxin, said DNA-binding domain, said promoter and said reporter gene so positioned that activation of said detectable gene occurs when said transcriptional activation domain of said second hybrid protein is in sufficient proximity to said detectable gene, said container comprising means for housing incubation of said host cell with said first and second vectors under conditions allowing either specific interaction between said first interacting protein and said second interacting protein or disruption of said protein—protein interaction in the presence of a test molecule which disrupts said protein—protein interaction.

14. The kit of claim 13 wherein said host cell is a eukaryotic cell.

15. The kit of claim 13 wherein said DNA-binding domain and transcriptional activation domain are derived from different transcriptional activators.

16. The kit of claim 15 wherein said transcriptional activators are bacterial, viral or eukaryotic.

* * * * *

UNITED STATES PATENT AND TRADEMARK OFFICE
CERTIFICATE OF CORRECTION

PATENT NO.   : 5,733,726

DATED        : March 31, 1998

INVENTOR(S)  : Fu et al.

It is certified that error appears in the above-identified patent and that said Letters Patent is hereby corrected as shown below:

On the cover page, column 1, under Other Publications, in the first listing "Wilson et al.", please change the first line so that "binding" is all together on the second line.

On the cover page, column 1, under Other Publications, in the third listing "Luban et al.", please delete "studyikng" and replace with --studying--.

On the cover page, column 2, under Other Publications, in the tenth listing "Fearon, E.R. et al.", please delete "interction" and replace with --interaction--.

On the cover page, column 2, under Other Publications, in the fourteenth listing "Harper, J.W. et al.", please delete "Calk-Interactinng" and replace with --Cdk-Interacting--.

In Column 1, line 60, please delete "contain a non-interacting" and replace with --contain non-interacting--.

In Column 2, line 4, please insert --USA-- after "Sci.".

In Column 2, line 7, please insert --USA-- after "Sci.".

In Column 4, line 2, please delete "represents" and replace with --represent--.

In Column 4, line 4, please delete "FIGS. 1A" and replace with --FIG. 1A--.

In Column 4, line 11, please delete "FIG. 2A-2C" and replace with --FIGS. 2A-2C--.

In Column 4, line 11, please delete "exemplifies" and replace with --exemplify--.

In Column 4, line 29, please delete "presents" and replace with --present--.

UNITED STATES PATENT AND TRADEMARK OFFICE
CERTIFICATE OF CORRECTION

PATENT NO. : 5,733,726

DATED : March 31, 1998

INVENTOR(S) : Fu et al.

It is certified that error appears in the above-identified patent and that said Letters Patent is hereby corrected as shown below:

In Column 7, line 35, please delete "Which" and replace with --which--.

In Column 7, line 37, please delete "(2D)" and replace with --(BD)--.

In Column 8, line 40, please delete "Cad." and replace with --Acad.--.

In Column 12, line 63, please delete "Mo." and replace with --Mol.--.

In Column 13, line 12, please delete "GAL1DTA" and replace with --GAL1-DTA--.

In Column 16, line 64, please delete "*and Shiga toxin*" and replace with --and Shiga toxin--.

Signed and Sealed this

Seventh Day of July, 1998

*Attest:*

BRUCE LEHMAN

*Attesting Officer*     *Commissioner of Patents and Trademarks*